US011819529B2

(12) United States Patent
Cao et al.

(10) Patent No.: US 11,819,529 B2
(45) Date of Patent: Nov. 21, 2023

(54) COMPOSITION FOR TREATING DIARRHEA

(71) Applicants: Tianjin Geonatural Technology Co., Ltd. (CN), Tianjin (CN); Jingjing Cao, Beijing (CN)

(72) Inventors: Jingjing Cao, Beijing (CN); Weiran Cui, Beijing (CN); Yueran Cui, Beijing (CN)

(73) Assignees: Tianjin Geonatural Technology Co., Ltd. (CN), Tianjin (CN); Jingjing Cao, Beijing (CN)

( * ) Notice: Subject to any disclaimer, the term of this patent is extended or adjusted under 35 U.S.C. 154(b) by 122 days.

(21) Appl. No.: 17/267,064

(22) PCT Filed: Aug. 8, 2019

(86) PCT No.: PCT/CN2019/000155
§ 371 (c)(1),
(2) Date: Feb. 9, 2021

(87) PCT Pub. No.: WO2020/029538
PCT Pub. Date: Feb. 13, 2020

(65) Prior Publication Data
US 2021/0161988 A1 Jun. 3, 2021

(30) Foreign Application Priority Data

Aug. 10, 2018 (CN) .......................... 201810909369.2
Aug. 10, 2018 (CN) .......................... 201810909377.7

(51) Int. Cl.
| | | |
|---|---|---|
| A61K 36/888 | (2006.01) | |
| A23L 33/00 | (2016.01) | |
| A23P 10/22 | (2016.01) | |
| A23L 29/00 | (2016.01) | |
| A23L 19/00 | (2016.01) | |
| A23L 33/15 | (2016.01) | |
| A61P 1/12 | (2006.01) | |
| A61K 36/23 | (2006.01) | |
| A61K 36/725 | (2006.01) | |
| A61K 36/73 | (2006.01) | |
| A61K 36/899 | (2006.01) | |
| A23L 13/10 | (2016.01) | |
| A23L 13/20 | (2016.01) | |
| A61K 35/407 | (2015.01) | |

(52) U.S. Cl.
CPC ............ *A61K 36/888* (2013.01); *A23L 13/10* (2016.08); *A23L 13/20* (2016.08); *A23L 19/01* (2016.08); *A23L 29/04* (2016.08); *A23L 33/15* (2016.08); *A23L 33/30* (2016.08); *A23P 10/22* (2016.08); *A61K 35/407* (2013.01); *A61K 36/23* (2013.01); *A61K 36/725* (2013.01); *A61K 36/73* (2013.01); *A61K 36/899* (2013.01); *A61P 1/12* (2018.01)

(58) Field of Classification Search
CPC .......... A23L 33/40; A23L 33/22; A23L 33/21; A23L 33/105; A23L 13/20; A23L 19/01; A23L 29/04; A23L 13/10; A23L 7/10; A23L 33/15; A23L 33/30; A61K 35/407; A61K 36/899; A61K 36/725; A61K 36/73; A61K 36/888; A61K 36/23; A61K 2300/00; A61K 300/00; A23P 10/22; A61P 1/12; A23V 2002/00; A23V 2200/32
See application file for complete search history.

(56) References Cited

U.S. PATENT DOCUMENTS

2016/0192683 A1    7/2016  Arnoff

FOREIGN PATENT DOCUMENTS

| CN | 1895454 A | | 1/2007 |
|---|---|---|---|
| CN | 104757420 A | | 7/2015 |
| CN | 105876327 A | | 8/2016 |
| CN | 106722963 A | * | 5/2017 |
| CN | 107361145 A | | 11/2017 |
| CN | 108013453 A | | 5/2018 |
| CN | 108904653 A | | 11/2018 |
| CN | 109090456 A | | 12/2018 |
| JP | 2008222822 A | | 9/2008 |

OTHER PUBLICATIONS

Brown AC, et al "The Medicinal Uses of Poi" Nutr Clin Care. 2004, 7(2), pp. 69-74. (Year: 2004).*
International Search Report and Non-Translated Written Opinion Form PCT/IS/210 and PCT/ISA/237, International Application No. PCT/CN2019/000155, pp. 1-8, International Filing Date Feb. 13, 2020, dated Nov. 7, 2019.
(Gu, Kuiqin) "(non-official translation: Paste of *Lablab purpureus* (L.) Sweet, Chinese Yam and Taro)" Jan. 31, 2003 (Jan. 3, 3003), p. 140, Paste of *Lablab Purpureus* (L.) Sweet, Chinese Yam and Taro.

(Continued)

*Primary Examiner* — Aaron J Kosar
(74) *Attorney, Agent, or Firm* — BOND SCHOENECK & KING, PLLC

(57) ABSTRACT

Disclosed in the present invention is a composition for treating diarrhea, comprising the following components calculated by weight ratio: *Colocasia esculenta* and antidiarrheal foods. The composition of the present invention has low cost, available raw materials, is safe and non-toxic, and is suitable for industrial production. The antidiarrheal effect of the product is remarkable. The rehabilitation time for the common diarrhea is 24-48 hours, and for the diarrhea caused by rotavirus is 48-72 hours, and the rehabilitation time is shortened by 2.5 days on average. The effective rate for persistent diarrhea within 5 days is 90.16%. For diarrhea of infants with milk protein allergy during the addition of supplementary feeding, six to eight kinds of foods can be added in one month, and thus the composition is especially suitable for infants and young children.

12 Claims, No Drawings

(56) References Cited

OTHER PUBLICATIONS (Zhang, Ming), "(non-offical translation: Taro Porridge)" (non-official translation: Encyclopedia of Healthy Rice Paste, Soy Milk and Miscellaneous Grain Porridge), Sep. 30, 2013 (Sep. 3, 2013), p. 209, Taro Porridge.

(Gan, Zhiron), "(non-officail translation: Red Dates and Taro)" 1688 (non-official translation: Grandma's Special Dishes 1688), Sep. 30, 2016 (Sep. 30, 2016), p. 149, Red Dates and Taro.

(Non-offical trnslation: Xlwen Books). "(non-offial translation: Soup Made with Coconut Juice, Carrot and Taro)" (non-official translation: Home Style Stewed Soup), Mar. 31, 2013 (2013-03031), p. 106 Soup Made with Coconut Juice, Carrot and Taro.

(Ge, Jing). "(non-offical translation: Sweet Water with Red Bean and Taro)" (Cereals Most Nourishes People), Jan. 31, 2014 (Jan. 31, 2014), p. 149, Sweet Water with Red Bean and Taro.

(non-official translation: Famous Teacher Culture). "(non-offical translation: Taro)" (non-official translation: Mild Vegetarian Diet), Mar. 31, 2014 (Mar. 31, 2014), p. 96, Reasonable Collocation.

(Yang, Guizhi et al.). "(non-official translation: Food suitable for Diarrhea Patients)" (non-offial translation: Diet and Health Care of Gastrointestinal Patients—Gastrointentinal Diseases Can Be Prevented and Treated), Apr. 30, 2013 (Apr. 30, 2013), p. 54 Food suitabel for Diarrhea Patients.

Refusal Notice, JP Application No. 2021-529501, dated Jan. 21, 2022, 5 pages.

Decision to Grant, JP Application No. 2021-529501, dated Aug. 10, 2022, 2 pages.

* cited by examiner

COMPOSITION FOR TREATING DIARRHEA

CROSS-REFERENCES TO RELATED APPLICATIONS

This is a National Stage Application, filed under 35 U.S.C. 371, of International Patent Application No. PCT/CN2019/000155, filed on Aug. 8, 2019, which is based on and claims priority to Chinese Patent Application No. 201810909369.2 filed with the CNIPA on Aug. 10, 2018, and Chinese Patent Application No. 201810909377.7 filed with the CNIPA on Aug. 10, 2018, the disclosure of each of which is incorporated herein by reference in its entirety.

TECHNICAL FIELD

The invention relates to a food composition for treating diarrhea, belonging to the food field.

BACKGROUND ART

*Colocasia esculenta*, also known as taro or Chinese eddo, is the underground bulb of *araceae* plants. Its shape and succulent vary from species to variety. The usually eaten species is small taro. Since taro contains a lot of dietary fiber, it also has a good laxative effect.

Some fruits and vegetables are rich in cellulose, which are also conducive to laxative; some fruits and vegetables contain a lot of sugars, which can form a hypertonic environment in the intestinal tract, which will further increase the water in the intestinal tract and aggravate diarrhea.

Cereals are rich in protein, starch and cellulose, and many of them are used for laxatives in daily life.

The above-mentioned raw materials are all daily food materials, and many of them belong to the medicine and food homologous substances. If these common ingredients are used to prepare drugs for treating diarrhea, side effects and adverse reactions will be greatly reduced, which is particularly important for infants and elderly patients.

Most infants and young children are weak or have other problems, and are prone to constipation and diarrhea. Clinically, medications for these groups are very cautious. At present, the clinical treatment of diarrhea for these groups has problems such as few types of drugs and high drug toxicity. The "Chinese Children's Clinical Practice Guidelines for Acute Infectious Diarrhea" clarified that eating early can improve the intestinal osmotic pressure caused by infection, shorten the course of diarrhea, and improve the nutritional status of children; a lactose-free diet can shorten the course of diarrhea in children with acute diarrhea. However, the Guidelines do not clearly indicate which foods to eat during diarrhea in children to help the intestinal recovery. Therefore, it is necessary to develop a safe and effective food for the treatment of infants and young children's diarrhea, through diet therapy, to achieve the purpose of alleviating diarrhea and supplementing nutrition to meet clinical needs.

CN201810909369.2 discloses a composition for regulating infant diarrhea. The composition has a good antidiarrheal effect on common infant infectious diarrhea, drug-induced diarrhea and food intolerance diarrhea, but has a poor effect on persisting diarrhea caused by severe milk protein allergy, lactose intolerance and inflammatory bowel disease (IBD). The effects of different formulas are quite different. Therefore, it is necessary to further optimize or design a new formula to solve the above problems.

CN108904653A discloses a pharmaceutical composition and uses thereof, which is composed of taro together with fruits and vegetables in a certain ratio. The composition has corresponding definitions on fruits and vegetables, but because part of the defined fruits and vegetables components are high-fiber plants, and it has been proved by practice that some raw materials have a diarrheal effect on infants and young children. Long-term consumption of the aforementioned foods, such as Chinese cabbage and radishes, during infants and young children's diarrhea, can aggravate diarrhea. Therefore, the components in the composition disclosed in CN108904653A have flawed technical defect that the antidiarrheal effect is unstable.

There is currently no safe and stable food for children on the market. Therefore, it is an urgent problem to develop a safe and effective antidiarrheal diet for infants and young children with safe food material as components.

SUMMARY OF THE INVENTION

The object of the present invention is to provide a dietary composition for treating diarrhea. The dietary composition uses common food materials as raw materials to achieve the purpose of antidiarrheal based on reasonable matching, which is safe and does not have side effects, so as to satisfy the need of antidiarrheal of frail people, such as infants and children as well as the patients with radiotherapy and chemotherapy.

Another object of the present invention is to provide a composition for treating diarrhea in infants with milk protein allergy, which can help infants with milk protein allergy to quickly solve the problem of supplementary food.

Another object of the present invention is to provide a composition for the treatment of persistent diarrhea caused by lactose intolerance and milk protein allergy, which can quickly and safely improve the symptoms of chronic diarrhea.

Another object of the present invention is to improve the technical solution disclosed in CN108904653A, so that the prepared composition can achieve better and more stable antidiarrheal effect.

In order to solve the above-mentioned problems, the components and ratio by weight of the pharmaceutical composition of the present invention comprise the taro and antidiarrheal food in combination to feed children with diarrhea. The combination can be operated according to ratio by volume or ratio by weight, preferably ratio by weight.

In the process of many years of dietary treatment of infants and children with diarrhea, the inventor has conducted continuous observations on the every meal feeding and daily excretion of more than 2000 children with diarrhea, especially those with milk protein allergy, from 2 months to 18 months. And after analyzing millions of pieces of data, the inventor found that some common foods have the function of restraining and stopping diarrhea in children's intestines. The antidiarrheal food of the present invention comprises the followings:

Vegetables include one or more selected from the group consisting of carrot (*Daucus carota*), broccoli (*Brassica oleracea* L. var. italic Planch.), cauliflower (*Brassica oleracea* L. var. botrytis L.), bok choy (*Brassica campestris* L. ssp. *chinensis* Makino var. *communis* Tsen et Lee), purple sweet potato (*Ipomoea batatas*, in color of purple or black), Chinese yam (*Dioscorea opposita*), lotus root (*Nelumbo nucifera*) and lotus seed (seed of *Nelumbo nucifera*, with core removed).

Meats include one or more selected from the group consisting of beef, pork liver and pork.

Fruits or nuts include one or more selected from the group consisting of cooked apple, chestnuts (*Castanea mollissima*) and jujube (*Ziziphus jujuba*).

Beans include small red bean (*Vigna angularis*) and/or azuki bean (*Vigna umbellata*).

Cereals include one or more selected from the group consisting of rice, glutinous rice (polished glutinous) and sorghum rice (polished sorghum).

The antidiarrheal food of the present invention can be one or more combinations in any ratio by weight. The antidiarrheal food can be made of fresh raw materials in a ratio by weight, or can be made into dry powder and then formulated.

In the composition of the present invention, preferably, the vegetables include one or more selected from the group consisting of carrot, broccoli, cauliflower, purple sweet potato, lotus root and lotus seed.

Fruits or nuts include one or more selected from the group consisting of cooked apple and jujube.

More preferably, the vegetables include one or more selected from the group consisting of carrot, broccoli, cauliflower and purple sweet potato.

Further preferably, the vegetables include one or two of carrot and purple sweet potato.

Furthermore preferably, the vegetable is carrot.

Preferably, the antidiarrheal food includes one or more selected from the group consisting of carrot, purple sweet potato, beef, chestnuts, jujube, small red bean, azuki bean, rice, glutinous rice and sorghum rice.

More preferably, the antidiarrheal food includes one or more selected from the group consisting of carrot, purple sweet potato, jujube, small red bean, azuki bean, rice, glutinous rice and sorghum rice.

Further preferably, the antidiarrheal food includes one or more selected from the group consisting of carrot, purple sweet potato, jujube, rice, glutinous rice and sorghum rice.

More preferably, the antidiarrheal food includes one or more selected from the group consisting of carrot, jujube, rice, glutinous rice and sorghum rice.

Furthermore preferably, the antidiarrheal food includes one or more selected from the group consisting of carrot, rice and glutinous rice.

Preferably, the taro is taro powder or taro puree; the antidiarrheal food is in a dry powder or pureed form.

The antidiarrheal foods of the present invention also comprises foods with astringent and antidiarrheal effects recorded in classical Chinese medicine books, such as "Huangdi Neijing", "Compendium of Materia Medica", "Shen Nong's Materia Medica", or other medicine and food homologous substances.

The components of the composition comprise powder, puree and granule; preferably powder. Powder of the raw material can be purchased from the open market or self-made.

The invention also discloses a method for the preparation of the composition, comprising:
(1) washing the taro, peeling, steaming, heating for 5 to 30 minutes after the water boils, and drying under 120° C. to make powder;
(2) washing the antidiarrheal food, cutting into pieces or pellets, boiling in water, continually heating for 5 to 30 minutes after the water boils, drying and crushing;
(3) mixing the taro powder and antidiarrheal food powder according to the ratio, and sterilizing to get the composition.

Preferably, the heating in step (1) is continued for 10 to 15 minutes after the water boils; the drying temperature is ≤100° C.; more preferably, the drying temperature is ≤80° C.

Preferably, the heating in step (2) is continued for 15 to 20 minutes after the water boils.

As the antidiarrheal food in the composition, commercially available ones can be selected.

When preparing the composition of the present invention, the drying method comprises roller drying, freeze drying and air drying.

The composition of the invention is suitable for viral diarrhea, bacterial diarrhea, allergic diarrhea, lactose intolerant diarrhea, drug-induced diarrhea, congenital megacolon diarrhea or inflammatory bowel disease (IBD) diarrhea.

1 to 7 grams each time for infants from 6 months to 36 months, 1 to 6 times a day; and 2 to 10 grams each time for children over 36 months old, 1 to 3 times a day.

The composition of the present invention has low cost, available raw materials, is safe and non-toxic, and is suitable for industrial production. The antidiarrheal effect of the product is remarkable. The rehabilitation time for common diarrhea is 24 to 48 hours, and for the diarrhea caused by rotavirus is 48 to 72 hours, and the rehabilitation time is shortened by 2.5 days on average. The effective rate for persistent diarrhea within 5 days is 90.16%. For diarrhea of infants with milk protein allergy during the addition of supplementary feeding, six to eight kinds of foods can be added in one month, and thus the composition is especially suitable for infants and young children.

BEST MODE OF THE INVENTION

The components and ratio by weight of the composition of the present invention comprise the taro and antidiarrheal food in combination to feed children with diarrhea. The combination can be operated according to volume ratio or ratio by weight, preferably ratio by weight. It can be confirmed that the composition of the present invention has a good antidiarrheal effect within the above-mentioned ratio. The following examples are merely illustrative, and do not intent to limit the protection scope of the present invention.

In the first embodiment of the present invention, taking 100 kg of taro and antidiarrheal food respectively, washing the taro, peeling, steaming, heating for 5 to 30 minutes after the water boils, and drying under 120° C. to make powder; washing the antidiarrheal food, cutting into pieces or pellets, boiling in water, continually heating for 5 to 30 minutes after the water boils, drying and crushing; mixing the taro powder and antidiarrheal food powder according to the ratio, and sterilizing to get the composition.

Preferably, when preparing the taro powder, heating is continued for 10 to 15 minutes after the water boils, and the drying temperature is ≤100° C.; more preferably, the drying temperature is ≤80° C.

Preferably, when preparing the antidiarrheal food powder, heating is continued for 15 to 20 minutes after the water boils.

In the second embodiment of the present invention, the taro powder and antidiarrheal food powder prepared in Example 1 are mixed according to the ratio by weight to prepare the composition of the present invention. Preferably, the taro and the antidiarrheal food are formulated according to the following ratio by weight: 10-90% taro and 10-90% antidiarrheal food; preferably, 10-85% taro and 15-90% antidiarrheal food; more preferably, 15-80% taro and 20-85% antidiarrheal food; further preferably, 25-75% taro and 25-75% antidiarrheal food; further preferably, 30-70% taro and 30-70% antidiarrheal food; further preferably, 35-65% taro and 35-65% antidiarrheal food; further preferably, 40-60% taro and 40-60% antidiarrheal food; more preferably, 50% taro and 50% antidiarrheal food.

Within the above-mentioned ratio ranges, the ratio of taro and antidiarrheal food by weight may be 90% taro and 10% antidiarrheal food; 10% taro and 90% antidiarrheal food; 85% taro and 15% antidiarrheal food; 80% taro and 20% antidiarrheal food; 75% taro and 25% antidiarrheal food; 70% taro and 30% antidiarrheal food; 65% taro and 35% antidiarrheal food; 60% taro and 40% antidiarrheal food; 55% taro and 45% antidiarrheal food; 45% taro and 55% antidiarrheal food; 40% taro and 60% antidiarrheal food, 35% taro and 65% antidiarrheal food; 30% taro and 70% antidiarrheal food; 25% taro and 75% antidiarrheal food; 20% taro and 80% antidiarrheal food; or 15% taro and 85% antidiarrheal food. The ratio of the taro and the antidiarrheal food by weight can also be any ratio between the weight percentages of the above groups, such as 60-65% taro and 35-40% antidiarrheal food; 33-64% taro and 36-67% antidiarrheal food, etc.

Preferably, the taro is taro puree; the antidiarrheal food is in a pureed form.

The antidiarrheal food of the present invention includes one or more selected from the group consisting of vegetables, meats, fruits or nuts, beans and cereals.

The vegetables include one or more selected from the group consisting of carrot, broccoli, cauliflower, bok choy, purple sweet potato, Chinese yam, lotus root and lotus seed (with core removed).

The meats include one or more selected from the group consisting of beef, pork liver and pork.

The fruits or nuts include one or more selected from the group consisting of cooked apple, chestnuts and jujube.

The beans include small red bean and/or azuki bean.

The cereals include one or more selected from the group consisting of rice, glutinous rice and sorghum rice.

The antidiarrheal food of the present invention can be one or more combinations in any ratio by weight.

Preferably, the antidiarrheal food includes one or more selected from the group consisting of carrot, purple sweet potato, beef, chestnuts, jujube, small red bean, azuki bean, rice, glutinous rice and sorghum rice.

More preferably, the antidiarrheal food includes one or more selected from the group consisting of carrot, purple sweet potato, jujube, small red bean, azuki bean, rice, glutinous rice and sorghum rice.

Further preferably, the antidiarrheal food includes one or more selected from the group consisting of carrot, purple sweet potato, jujube, rice, glutinous rice and sorghum rice.

More preferably, the antidiarrheal food includes one or more selected from the group consisting of carrot, jujube, rice, glutinous rice and sorghum rice.

Furthermore preferably, the antidiarrheal food includes one or more selected from the group consisting of carrot, rice and glutinous rice.

The raw materials in each component in this embodiment can be combined arbitrarily, and each component can be formulated within a limited range, and the final prepared composition has the same antidiarrheal effect.

In the third embodiment of the present invention, the taro powder and antidiarrheal food powder prepared in Example 1 are mixed according to the ratio by weight to prepare the composition of the present invention. The antidiarrheal foods are combined according to a certain ratio by weight, and the ratio comprises the followings:

10-70% vegetables, 5-30% meats, 5-60% fruits or nuts, 10-60% beans, and 10-70% cereals;

preferably, 20-40% vegetables, 10-20% meats, 10-40% fruits or nuts, 10-40% beans, and 20-40% cereals;

more preferably, 30% vegetables, 10% meats, 10% fruits or nuts, 20% beans, and 30% cereals.

In the composition of the present invention, preferably, the vegetables comprise one or more selected from the group consisting of carrot, broccoli, cauliflower, purple sweet potato, lotus root and lotus seed (with core removed).

The meats include one or more selected from the group consisting of beef, pork liver and pork.

The fruits or nuts include one or more selected from the group consisting of cooked apple and jujube.

The beans include small red bean and/or azuki bean.

The cereals include one or more selected from the group consisting of rice, glutinous rice and sorghum rice.

More preferably, the vegetables include one or more selected from the group consisting of carrot, broccoli, cauliflower and purple sweet potato.

Further preferably, the vegetables include one or two of carrot and purple sweet potato.

Furthermore preferably, the vegetable is carrot.

Within the above-mentioned ratio ranges, the ratio of the antidiarrheal food by weight may be 60% carrot, 10% beef, 5% jujube, 10% small red bean, and 15% rice; 30% broccoli, 15% pork, 25% steamed apple, 15% azuki bean, and 15% glutinous rice; 25% carrot and purple sweet potato, 10% beef, 20% jujube, 18% small red bean and azuki bean, and 27% rice and glutinous rice; 15% lotus seed, 20% pork liver, 15% jujube and cooked apple, 20% azuki bean, and 30% sorghum rice; or 30% carrot, 10% beef, 10% jujube, 20% small red bean, and 30% rice.

The raw materials in each component in this embodiment can be combined arbitrarily, and each component can be formulated within a limited range, and the final prepared composition has the same or similar antidiarrheal effect.

In the fourth embodiment of the present invention, the types of antidiarrheal foods are further limited. The antidiarrheal food is made of vegetables, fruits or nuts, beans and cereals in a ratio by weight. The ratio of the antidiarrheal food by weight comprises the followings:

10-75% vegetables, 5-60% fruits or nuts, 10-60% beans, and 10-75% cereals.

Preferably, 10-60% vegetables, 10-40% fruits or nuts, 20-50% beans, and 10-60% cereals.

More preferably, 20-40% vegetables, 20-40% fruits or nuts, 20-40% beans, and 20-40% cereals.

Further preferably, 30% vegetables, 20% fruits or nuts, 20% beans, and 30% cereals.

In the composition of the present invention, preferably, the vegetables include one or more selected from the group consisting of carrot, broccoli, cauliflower, purple sweet potato, lotus root and lotus seed.

The fruits or nuts include one or more selected from the group consisting of cooked apple and jujube.

More preferably, the vegetables include one or more selected from the group consisting of carrot, broccoli, cauliflower and purple sweet potato.

Further preferably, the vegetables include one or two of carrot and purple sweet potato.

More preferably, the vegetable is carrot.

In this embodiment, the antidiarrheal food components remove the meat component. During the experiment, the inventor found that a small number of children with diarrhea had indigestion of meats, especially children with infectious diarrhea, so a vegetarian formula is applied.

The ratio of the components by weight comprises the followings: 40% cauliflower and purple sweet potato, 15% jujube, 25% small red bean, and 20% rice and glutinous rice; 30% carrot, 20% steamed apple, 20% azuki bean, and 30% glutinous rice; 25% carrot and purple sweet potato, 20% jujube, 25% small red bean and azuki bean, and 30% sorghum rice; 20% lotus root, 20% jujube and cooked apple, 30% azuki bean, and 30% glutinous rice; or 30% carrot, 20% jujube, 20% red bean, and 30% rice.

Of course, in addition to the specific proportions mentioned above, the raw materials in each component in this embodiment can be combined arbitrarily, and each component can be formulated within a limited range, and the final prepared composition has the same or similar antidiarrheal effect.

In the fifth embodiment of the present invention, the antidiarrheal food is made of vegetables and cereals in a ratio by weight. The ratio of the antidiarrheal food by weight comprises the followings:

10-90% vegetables and 10-90% cereals.

Preferably, 25-75% vegetables and 25-75% cereals.

More preferably, 30-70% vegetables and 30-70% cereals.

Further preferably, 40-60% vegetables and 40-60% cereals.

Furthermore preferably, 50% vegetables and 50% cereals.

In the composition of the present invention, preferably, the vegetables include one or more selected from the group consisting of carrot, broccoli, cauliflower, purple sweet potato, lotus root and lotus seed.

More preferably, the vegetables include one or more selected from the group consisting of carrot, broccoli, cauliflower and purple sweet potato.

Further preferably, the vegetables include one or two of carrot and purple sweet potato.

More preferably, the vegetable is carrot.

In this embodiment, the inventor found that a small number of children are allergic to beans. If the peels of fruits or nuts are not completely removed, the digestive tract may also be affected. Therefore, the components of the product are further reduced, and the types of antidiarrheal foods are limited to vegetables and cereals.

The ratio of the components by weight comprises the followings: 80% carrot and 20% rice; 90% broccoli and carrot, and 10% glutinous rice; 25% purple sweet potato, and 75% rice and glutinous rice; 40% lotus seed, and 60% sorghum rice and glutinous rice; 45% cauliflower and broccoli, and 55% rice; 50% carrot and purple sweet potato, and 50% rice and glutinous rice, etc.

Of course, in addition to the specific proportions mentioned above, the raw materials in each component in this embodiment can be combined arbitrarily, and each component can be formulated within a limited range, and the final prepared composition has the same or similar antidiarrheal effect.

In the sixth embodiment of the present invention, in order to meet the need of growth and development of infants and young children, the trace elements and minerals can be added to the composition of the present invention to prepare a complete nutritional formula.

Preferably, the energy per 100 g of the composition is $\geq 1250$ kJ; the nutrients per 100 kJ include:

protein$\geq 0.33$ g, fat$\leq 0.8$ g, vitamin A 14-43 µgRE, vitamin D 0.25-0.75 µg, vitamin B1$\geq 12.5$ µg, calcium$\geq 12$ mg, iron 0.25-0.5 mg, zinc$\geq 0.17$-0.46 mg, and sodium$\leq 24$ mg;

the following contents of vitamins and minerals can also be added to the composition:

vitamin E 0.08-1.2 mg, vitamin B2$\geq 13$ µg, vitamin B6$\geq 8.4$ µg, vitamin B12$\geq 0.02$ µg, niacin$\geq 83.7$ µg, folic acid$\geq 1.2$ µg, pantothenic acid$\geq 50.4$ µg, vitamin C$\geq 1.4$ mg, biotin$\geq 0.17$ µg, phosphorus 8.4-30 mg, iodine 1.4-8.8 µg, and potassium 13-66 mg.

More preferably, in order to further meet the need of growth and development of infants under 1 year old during diarrhea, the nutrients and contents contained per 100 kJ in the composition of the present invention comprise: protein 0.45-0.7 g, fat 1.05-1.4 g, carbohydrate 2.2-3.3 g, vitamin A 14-43 µgRE, vitamin D 0.25-0.6 µg, vitamin E 0.12-1.2 mg, vitamin K1 1.0-6.5 µg, vitamin B1 14-72 µg, vitamin B2 19-119 µg, vitamin B6 8.5-45 µg, vitamin B12 0.02-0.36 µg, niacin 70-360 µg, folic acid 2.5-12 µg, pantothenic acid 96-478 µg, vitamin C 2.5-17 mg, biotin 0.4-2.4 µg, sodium 5-14 mg, potassium 14-43 mg, copper 8.5-29 µg, magnesium 1.2-3.6 mg, iron 0.1-0.36 mg, zinc 0.12-0.36 mg, manganese 1.2-24 µg, calcium 12-35 mg, phosphorus 6-24 mg, the ratio of calcium to phosphorus 1:1-2:1, iodine 2.5-14 µg, chlorine 12-38 mg, and selenium 0.48-1.9 µg;

preferably, the following contents of trace elements can also be added to the composition:

chromium 0.4-2.4 µg, molybdenum 0.4-2.4 µg, choline 1.7-12 mg, inositol 1-9.5 mg, taurine$\leq 3$ mg, L-carnitine$\geq 0.3$ mg, docosahexaenoic acid (% of total fatty acids)$\leq 0.5$, and eicosatetraenoic acid (% of total fatty acids)$\leq 1$.

Further preferably, in order to further meet the need of growth and development of children over 1 year old during diarrhea, the nutrients and content contained per 100 kJ in the composition of the present invention include: vitamin A 17.9-58.3 µgRE, vitamin D 0.25-0.75 µg, vitamin E$\geq 0.15$ mg, vitamin K1$\geq 1$ µg, vitamin B1$\geq 0.01$ mg, vitamin B2$\geq 0.01$ mg, vitamin B6$\geq 0.01$ mg, vitamin B12$\geq 0.04$ µg, niacin$\geq 0.11$ mg, folic acid$\geq 1$ µg, pantothenic acid$\geq 0.07$ mg, vitamin C$\geq 1.8$ mg, biotin$\geq 0.4$ µg, sodium 5-20 mg, potassium 18-69 mg, copper 7-35 µg, magnesium$\geq 1.4$ mg, iron 0.25-0.5 mg, zinc 0.1-0.4 mg, manganese 0.3-24 µg, calcium$\geq 17$ mg, phosphorus 8.3-46.2 mg, the ratio of calcium to phosphorus 1:1-2:1, iodine$\geq 1.4$ µg, chlorine$\leq 52$ mg, and selenium 0.5-2.9 µg;

further preferably, the following content of trace elements can also be added to the composition: chromium 0.4-5.7 µg, molybdenum 1.2-5.7 µg, fluorine$\leq 0.05$ mg, choline 1.7-19.1 mg, inositol 1-9.5 mg, taurine$\leq 3.1$ mg, L-carnitine$\geq 0.3$ mg, docosahexaenoic acid (% of total fatty acids)$\leq 0.5$, eicosatetraenoic acid (% of total fatty acids)$\leq 1$, nucleotides$\geq 0.5$ mg, and dietary fiber$\leq 0.7$ g.

The components of the composition comprise powder, puree form and granule; preferably powder. The powder of raw material can be purchased from the open market or self-made.

3.5 to 7 grams each time for infants from 6 months to 3 years old, 2 to 3 times a day; and 5 to 10 grams each time for children over 36 months old, 2 to 3 times a day.

The composition of the present invention is suitable for the treatment and nutritional support of viral diarrhea, bacterial diarrhea, allergic diarrhea, lactose intolerant diarrhea, drug-induced diarrhea, congenital megacolon diarrhea or inflammatory bowel disease (IBD) diarrhea.

The pharmaceutical composition of the present invention has obvious antidiarrheal function. Those skilled in the art can change the components through equivalent substitutions, etc., but all fall within the protection scope of the present invention.

TEST EXAMPLE

Experimental Example 1. Clinical Observation of the Composition of the Present Invention in Treating Viral Diarrhea 1. Clinical Data 1.1 General information. 108 children outpatients with diarrhea were randomly divided into treatment group (54 cases) and control group (54 cases). All cases had obvious dehydration before treatment, and the number of diarrhea in 24 hours was more than 5 times. There were 54 cases in the treatment group, including 31 boys and 23 girls, aged 1 to 5 years old, with an average of 2.7 years old. There were 54 cases in the control group, including 34 boys and 20 girls, aged from 1 to 4.8 years old, with an average of 2.4 years old. After statistical processing, the clinical data of the two groups are comparable ($P>0.05$).

1.2 Treatment methods. The two groups were given symptomatic treatment such as rehydration. The treatment group orally took the composition prepared in Example 2 of the present invention with 50% taro, 25% carrot, 25% rice and glutinous rice in the ratio by weight. For infants with diarrhea from 6 months to 3 years old, 3.5 grams of the pharmaceutical composition were rinsed with warm water and taken orally, 6 times a day. For children with diarrhea over 3 years old, 7 grams the pharmaceutical composition were rinsed with warm water and taken orally, 3 times a day. Taking for 3 consecutive days is one course of treatment. The frequency and severity of diarrhea were observed, and routine blood tests, urine tests, liver function tests and kidney function tests were carried out before and after treatment. The control group took the eight-sided montmorillonite powder orally according to the method and dosage of the instructions.

1.3 The standardization of efficacy evaluation is based on "Diagnostic Criteria and Principles of Treatment of Infectious Diarrhea". Significantly effective: diarrhea frequency in 24 h≤2 times; Effective: 3 times≤diarrhea frequency in 24 h≤5 times; and Ineffective: diarrhea frequency in 24 h>5 times, the diarrhea frequency is not significantly reduced or excreting watery stools.

2. Results 2.1 Comparison of the treatment effect for diarrhea between the two groups is shown in Table 1.

TABLE 1

Comparison of the treatment effect for diarrhea between the two groups

| Groups | Cases | Significantly Effective n | % | Effective n | % | Ineffective n | % | Total effective rate % |
|---|---|---|---|---|---|---|---|---|
| Treatment group | 54 | 49 | 90.74 | 4 | 7.41 | 1 | 1.85 | 98.15 |
| Control Group | 54 | 43 | 79.63 | 6 | 11.11 | 5 | 9.26 | 90.74 |

3. Discussion

Both the composition of the present invention and the control group have the effects of treating diarrhea and constricting the intestinal tract. The effect of the composition group of the invention is better than that of the control group.

Experimental Example 2. Clinical Observation of the Pharmaceutical Composition of the Present Invention in Treating Diarrhea Caused by Lactose Intolerance and Milk Protein Allergy Diarrhea in Infants and Children 1. Clinical Data 1.1 General information. 100 outpatients with persistent diarrhea caused by lactose intolerance and milk protein allergy were randomly divided into treatment group (50 cases) and control group (50 cases). There were 80 children with lactose intolerance and persistent diarrhea, 60 children with milk protein allergy, and 40 children with milk protein allergy and lactose intolerance. All cases had symptoms of diarrhea after consuming breast milk or hydrolyzed formula powder containing lactose before treatment. Diarrhea occurred half an hour after breastfeeding and was detected as lactose intolerance and/or milk protein allergy. There were 50 cases in the treatment group, including 35 boys and 15 girls, aged from 6 months to 3 years old, with an average of 1.6 years old. There were 50 cases in the control group, including 26 boys and 24 girls, aged from 7 months to 2.5 years old, with an average age of 1.4 years old. After statistical processing, the clinical data of the two groups are comparable ($P>0.05$).

1.2 Therapeutic method. The treatment group orally took the composition prepared in Example 2 of the present invention with 25% taro, 20% carrot, 30% rice and 25% glutinous rice in the ratio by weight. For infants with diarrhea from 6 months to 3 years old, 3.5 grams of the pharmaceutical composition were rinsed with warm water and taken orally, 6 times a day. For children with diarrhea over 3 years old, 7 grams the pharmaceutical composition were rinsed with warm water and taken orally, 3 times a day. Taking for 5 consecutive days is one course of treatment. The frequency of diarrhea was observed before and after treatment. The control group orally took lactase according to the method and dosage of the instructions.

1.3 The standardization of efficacy evaluation. Significantly effective: diarrhea frequency in 4 hours after feeding≤1 time; Effective: 1 time<diarrhea frequency in 4 hours after feeding≤2 times; and Ineffective: diarrhea frequency in 4 hours after feeding≥3 times, the diarrhea frequency is not significantly reduced or there is no obvious reduction in watery stools.

2. Results 2.1 Comparison of the treatment effect for diarrhea between the two groups is shown in Table 2.

TABLE 2

Comparison of the treatment effect for diarrhea between the two groups

| Groups | Cases | Significantly Effective n | % | Effective n | % | Ineffective n | % | Total effective rate % |
|---|---|---|---|---|---|---|---|---|
| Treatment group | 50 | 37 | 74.00 | 11 | 22.00 | 2 | 4.00 | 96.00 |
| Control Group | 50 | 28 | 56.00 | 13 | 26.00 | 9 | 18.00 | 82.00 |

3. Discussion

Both the composition of the present invention and the control group have the effects of treating diarrhea caused by lactose intolerance and milk protein allergy and constricting the intestinal tract. The effect of the composition group of the invention is better than that of the control group.

What is claimed is:

1. A composition for treating diarrhea, comprising taro and antidiarrheal food; wherein the antidiarrheal food comprises vegetables and cereals;
the vegetables comprise carrot;
the cereals comprise one or more selected from the group consisting of rice, and glutinous rice; and
based on the composition, the ratio of the taro by weight is 10-90% and based on the antidiarrheal food, the ratio of the vegetables by weight is 10-90% and the ratio of the cereals by weight is 10-90%; and
wherein the taro and antidiarrheal food are powder, puree, or granule form.

2. The composition according to claim 1, wherein based on the composition, the ratio of the taro by weight is 25-75%, and based on the antidiarrheal food, the ratio of the vegetables by weight is 25-75% and the ratio of the cereals by weight is 25-75%.

3. The composition according to claim 1 or 2, wherein based on the composition, the ratio of the taro by weight is 30-70%, and based on the antidiarrheal food, the ratio of the vegetables by weight is 30-70% and the ratio of the cereals by weight is 30-70%.

4. The composition according to claim 1 or 2, wherein based on the composition, the ratio of the taro by weight is 40-60%, and based on the antidiarrheal food, the ratio of the vegetables by weight is 40-60% and the ratio of the cereals by weight is 40-60%.

5. The composition according to claim 1 or 2, wherein based on the composition, the ratio of the taro by weight is 50%, and based on the antidiarrheal food, the ratio of the vegetables by weight is 50% and the ratio of the cereals by weight is 50%.

6. The composition according to claim 1 or 2, wherein based on the composition, the ratio of the taro by weight is 25%, the ratio of the vegetables by weight is 20% and the ratio of the cereals by weight is 55%.

7. The composition according to claim 1 or 2, wherein trace elements with following contents are added to the composition:
the energy per 100 g of the composition is ≥1250 kJ; the nutrients per 100 kJ comprise: protein≥0.33 g, fat≤0.8 g, vitamin A 14-43 µgRE, vitamin D 0.25-0.75 µg, vitamin B1≥12.5 µg, calcium≥12 mg, iron 0.25-0.5 mg, zinc≥0.17-0.46 mg, and sodium≤24 mg.

8. The composition of claim 1, wherein the composition further comprises:
vitamin E 0.08-1.2 mg, vitamin B2≥13 µg, vitamin B6≥8.4 µg, vitamin B12≥0.02 µg, niacin≥83.7 µg, folic acid≥1.2 µg, pantothenic acid≥50.4 µg, vitamin C≥1.4 mg, biotin≥0.17m, phosphorus 8.4-30 mg, iodine 1.4-8.8 µg, and potassium 13-66 mg.

9. The composition of claim 1, wherein the nutrients and contents contained per 100 kJ in the composition comprise: protein 0.45-0.7 g, fat 1.05-1.4 g, carbohydrate 2.2-3.3 g, vitamin A 14-43 µgRE, vitamin D 0.25-0.6 µg, vitamin E 0.12-1.2 mg, vitamin K1 1.0-6.5 µg, vitamin B1 14-72 µg, vitamin B2 19-119 µg, vitamin B6 8.5-45 µg, vitamin B12 0.02-0.36 µg, niacin 70-360 µg, folic acid 2.5-12 µg, pantothenic acid 96-478 µg, vitamin C 2.5-17 mg, biotin 0.4-2.4 µg, sodium 5-14 mg, potassium 14-43 mg, copper 8.5-29 µg, magnesium 1.2-3.6 mg, iron 0.1-0.36 mg, zinc 0.12-0.36 mg, manganese 1.2-24 µg, calcium 12-35 mg, phosphorus 6-24 mg, the ratio of calcium to phosphorus 1:1-2:1, iodine 2.5-14 µg, chlorine 12-38 mg, and selenium 0.48-1.9 µg.

10. The composition of claim 1, wherein the composition further comprises:
chromium 0.4-2.4 µg, molybdenum 0.4-2.4 µg, choline 1.7-12 mg, inositol 1-9.5 mg, taurine≤3 mg, L-carnitine≥0.3 mg, docosahexaenoic acid % of total fatty acids≤0.5%, and eicosatetraenoic acid % of total fatty acids≤1%.

11. The composition of claim 1, wherein the nutrients and content contained per 100 kJ in the composition comprise: vitamin A 17.9-58.3 µgRE, vitamin D 0.25-0.75 µg, vitamin E≥0.15 mg, vitamin K1≥1 µg, vitamin B1≥0.01 mg, vitamin B2≥0.01 mg, vitamin B6≥0.01 mg, vitamin B12≥0.04 µg, niacin≥0.11 mg, folic acid≥1 µg, pantothenic acid≥0.07 mg, vitamin C≥1.8 mg, biotin≥0.4 µg, sodium 5-20 mg, potassium 18-69 mg, copper 7-35 µg, magnesium≥1.4 mg, iron 0.25-0.5 mg, zinc 0.1-0.4 mg, manganese 0.3-24 µg, calcium≥17 mg, phosphorus 8.3-46.2 mg, the ratio of calcium to phosphorus 1:1-2:1, iodine≥1.4 µg, chlorine≤52 mg, and selenium 0.5-2.9 µg.

12. The composition of claim 1, wherein the following contents of trace are added to the composition: chromium 0.4-5.7 µg, molybdenum 1.2-5.7 µg, fluorine≤0.05 mg, choline 1.7-19.1 mg, inositol 1-9.5 mg, taurine≤3.1 mg, L-carnitine≥0.3 mg, docosahexaenoic acid % of total fatty acids≤0.5, eicosatetraenoic acid % of total fatty acids≤1, nucleotides≥0.5 mg, and dietary fiber≤0.7 g.

* * * * *